(12) United States Patent
Fritzinger

(10) Patent No.: US 8,133,235 B2
(45) Date of Patent: Mar. 13, 2012

(54) ONE-WAY BEARING CABLE TENSIONING TOOL

(75) Inventor: Daniel D. Fritzinger, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 135 days.

(21) Appl. No.: 12/576,491

(22) Filed: Oct. 9, 2009

(65) Prior Publication Data
US 2011/0087225 A1 Apr. 14, 2011

(51) Int. Cl.
*A61B 17/58* (2006.01)
(52) U.S. Cl. .................... 606/103; 242/376
(58) Field of Classification Search .......... 606/139–141, 606/144–146, 148–150, 263, 74, 86 R, 99, 606/103, 300; 29/894.2; 211/85.5; 242/227, 242/370, 295, 376, 382, 385, 600, 18
See application file for complete search history.

(56) References Cited

U.S. PATENT DOCUMENTS

| | | | | |
|---|---|---|---|---|
| 440,812 A | * | 11/1890 | Keats | 242/118 |
| 3,008,664 A | * | 11/1961 | McCormick | 242/405.1 |
| 4,966,600 A | * | 10/1990 | Songer et al. | 606/74 |
| 5,116,340 A | | 5/1992 | Songer et al. | |
| 5,397,073 A | * | 3/1995 | Fujimura | 242/376 |
| 5,536,270 A | | 7/1996 | Songer et al. | |
| 5,649,927 A | | 7/1997 | Kilpela et al. | |
| 5,693,046 A | * | 12/1997 | Songer et al. | 606/74 |
| 5,741,260 A | * | 4/1998 | Songer et al. | 606/74 |
| 5,752,959 A | | 5/1998 | Korhonen | |
| 5,788,697 A | | 8/1998 | Kilpela et al. | |
| 5,935,130 A | | 8/1999 | Kilpela et al. | |
| 6,066,141 A | | 5/2000 | Dall et al. | |
| 6,364,885 B1 | | 4/2002 | Kilpela et al. | |
| 6,416,003 B1 | * | 7/2002 | Wier | 242/376 |
| 6,595,994 B2 | | 7/2003 | Kilpela et al. | |
| 6,780,198 B1 | * | 8/2004 | Gregoire et al. | 606/232 |
| 6,832,532 B2 | | 12/2004 | Kilpela et al. | |
| 7,862,582 B2 | * | 1/2011 | Ortiz et al. | 606/216 |
| 2005/0033364 A1 | * | 2/2005 | Gregoire et al. | 606/232 |
| 2008/0281336 A1 | * | 11/2008 | Zergiebel | 606/142 |
| 2009/0008205 A1 | * | 1/2009 | Ishida | 192/45 |
| 2009/0069823 A1 | * | 3/2009 | Foerster et al. | 606/139 |
| 2010/0286714 A1 | * | 11/2010 | Gyrn et al. | 606/139 |
| 2011/0028997 A1 | * | 2/2011 | Gregoire et al. | 606/144 |

OTHER PUBLICATIONS

Web Article—Principles and Application of Cerclage Wire Full and Hemicerclage Wiring, Roger Clarke, 28th World Congress of the World Small Animal Veterinary Association, Oct. 24-27, 2003 Bangkok, Thailand.
Product Brochure—Cable Grip System, Comprehensive Cable Grip System, Family Ties, Zimmer, 2001, 97-2232-2001 20ML.
Surgical Technique—Cable Grip System, Zimmer, 1997, 97-2232-08 10MZ.
Abbreviated Surgical Technique, Cable-Ready Bone Plate, Integral crimp for secure low profile implant, Zimmer, 1999, 2001, 2005, 97-2232-105-00 Rev. 2 5MM.
Surgical Technique, Cable-Ready Greater Trochanteric Reattachment, Stabilization of the Greater Trochanter, Zimmer, 2001, 2006, 97-2232-107-00 Rev. 1 5ML.

* cited by examiner

*Primary Examiner* — Eduardo C Robert
*Assistant Examiner* — Stuart S Bray
(74) *Attorney, Agent, or Firm* — Faegre Baker Daniels

(57) ABSTRACT

An orthopedic tool having a one-way lock bearing and a one-way actuator bearing for tensioning surgical cables around a bone and a method for using the same.

14 Claims, 7 Drawing Sheets

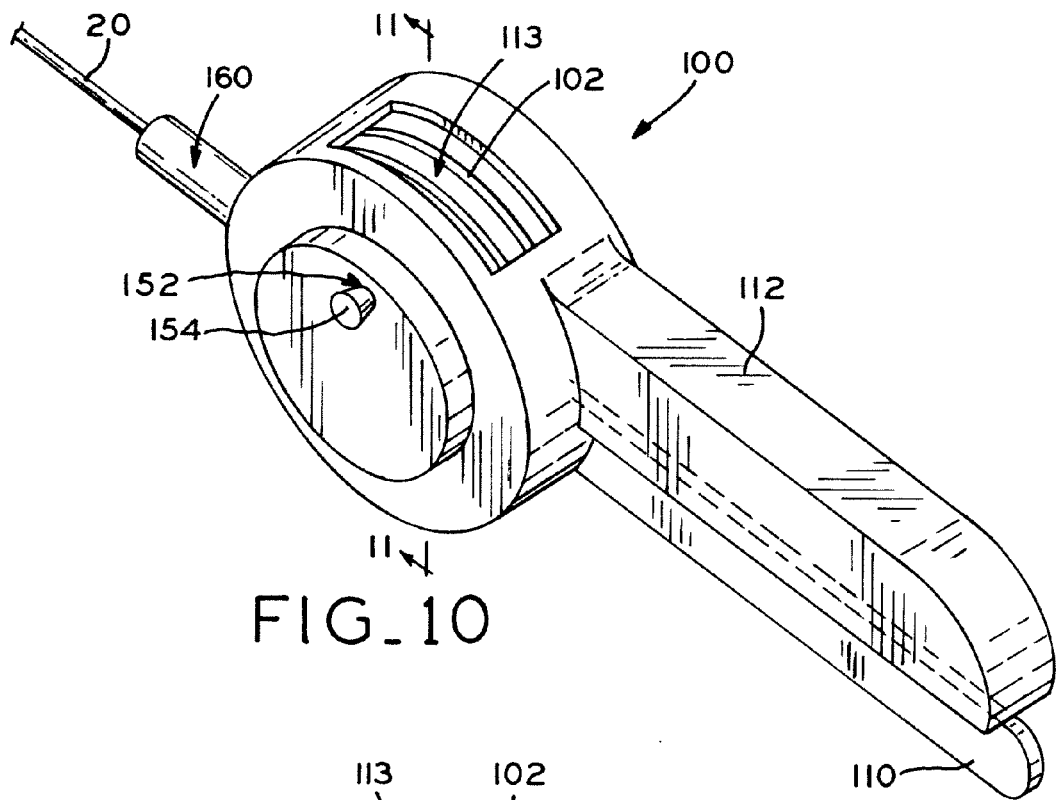
FIG._10
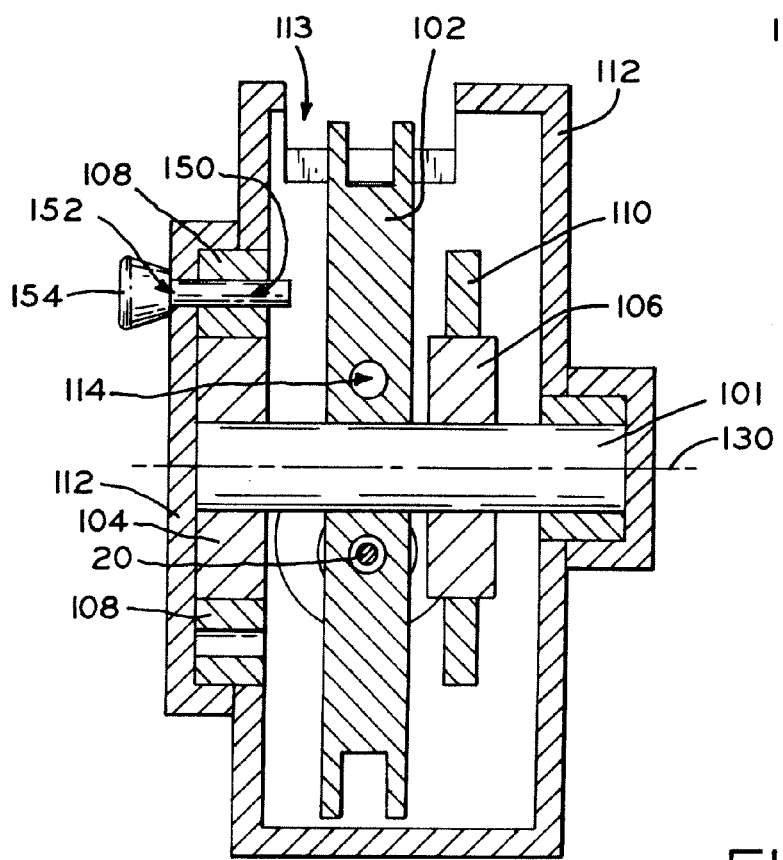
FIG._11

ONE-WAY BEARING CABLE TENSIONING TOOL

BACKGROUND

1. Field of the Invention

The present invention relates to an orthopedic tool. More particularly, the present invention relates to an orthopedic tool for tensioning surgical cables, and to a method for using the same.

2. Description of the Related Art

To stabilize a fractured bone, an orthopedic bone plate may be secured against the bone and extend across the fracture line. The bone plate may be anchored onto the fractured bone using bone screws. Also, the bone plate may be tied onto the fractured bone using surgical cables.

SUMMARY

The present invention provides an orthopedic tool having a one-way lock bearing and a one-way actuator bearing for tensioning surgical cables around a bone and a method for using the same.

According to an embodiment of the present invention, a tool is provided for tensioning a surgical cable around a bone. The tool includes a housing, a shaft, a drum, a lock bearing, and an actuator bearing. The drum is coupled to the shaft for rotation therewith relative to the housing, the shaft configured to rotate in a first winding direction to wind the surgical cable around the drum and in a second unwinding direction to unwind the surgical cable from the drum. The lock bearing is coupled to the shaft and configured to prevent the shaft from rotating in the second unwinding direction relative to the housing. The actuator bearing is coupled to the shaft and configured to rotate the shaft in the first winding direction.

According to another embodiment of the present invention, a tool is provided for tensioning a surgical cable around a bone. The tool includes a drum configured to rotate in a first winding direction to wind the surgical cable around the drum and in a second unwinding direction to unwind the surgical cable from the drum, the drum defining a plurality of internal channels configured to receive the surgical cable therein. The tool also includes means for preventing the drum from rotating in the second unwinding direction and means for rotating the drum in the first winding direction.

According to yet another embodiment of the present invention, a method is provided for tensioning a surgical cable around a bone. The method includes the steps of: providing a tensioning tool including a shaft, a drum coupled to the shaft, a lock bearing coupled to the shaft, and an actuator bearing coupled to the shaft; wrapping the surgical cable around the bone; operating the actuator bearing to rotate the shaft in a first winding direction to wind the surgical cable onto the drum; and locking the lock bearing to prevent the shaft from rotating in a second unwinding direction to unwind the surgical cable from the drum.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 10 is a left-side perspective view of another exemplary tensioning tool of the present invention, including a housing having a window; and FIG. 11 is a cross-sectional view of the tensioning tool of FIG. 10, taken along line 11-11 of FIG. 10.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
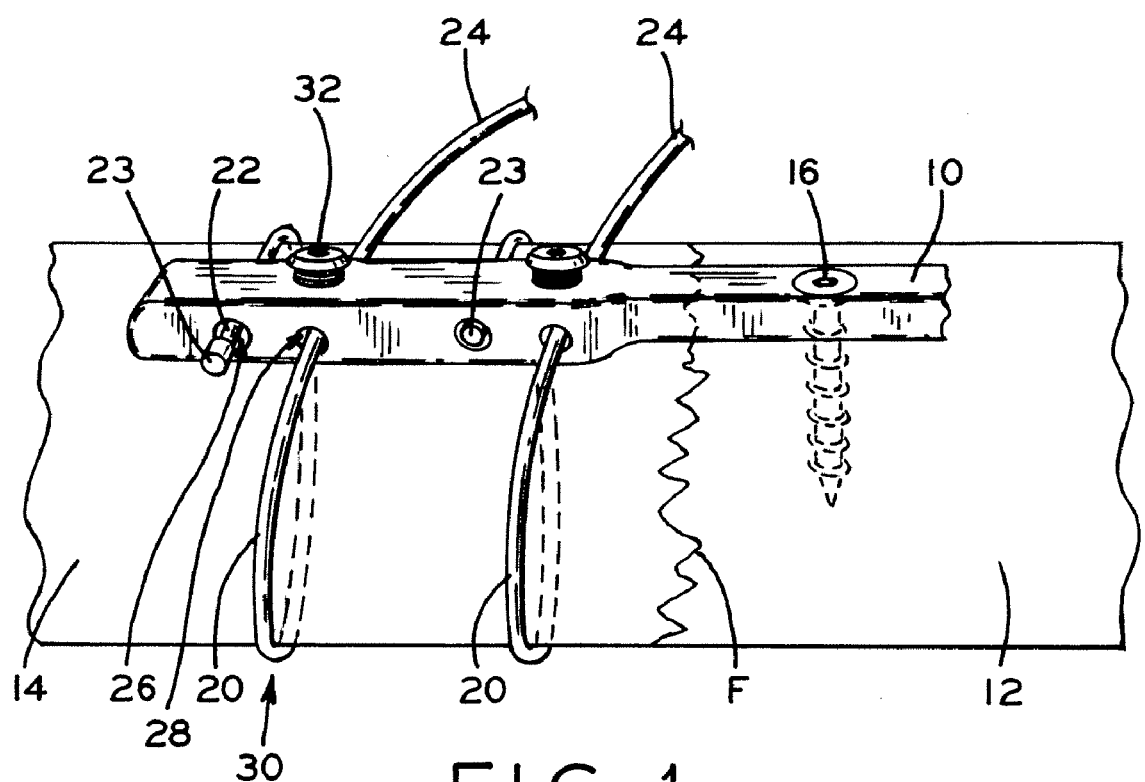
FIG. 1 is a perspective view of a bone plate secured to a fractured bone using surgical cables and a bone screw.
Figure 2:
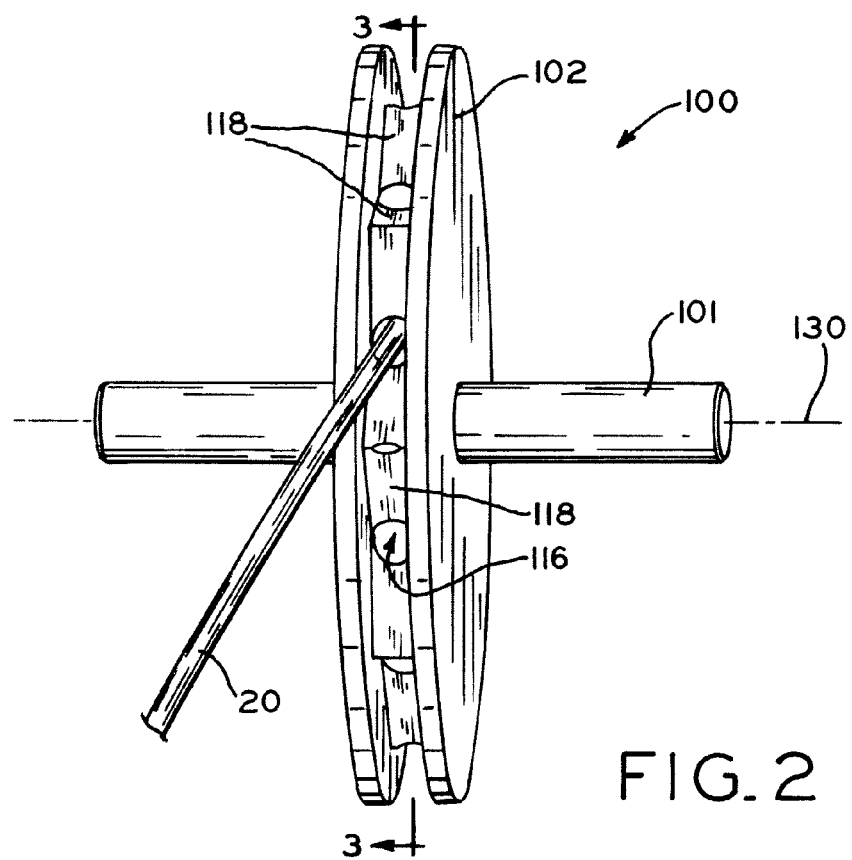
FIG. 2 is a perspective view of an exemplary tensioning tool of the present invention for tensioning the surgical cable of FIG. 1, the tensioning tool including a winding drum coupled to a shaft.

FIG. 1 illustrates an orthopedic assembly in the form of bone plate 10 that is secured to a fractured bone 12 across fracture F. More particularly, bone plate 10 is secured to shaft 14 of fractured bone 12 across fracture F. Bone 12 may include a patient's femur, tibia, fibula, radius, ulna, clavicle, or another bone. Although bone plate 10 is described and depicted herein as extending across fracture F in bone 12, bone plate 10 may also be used as part of a dynamic hip system to anchor a fractured femoral head to a femoral shaft, for example, or as part of another suitable orthopedic assembly.

Bone plate 10 may be secured to bone 12 with a variety of anchors and/or fasteners. As shown in FIG. 1, bone plate 10 is secured to bone 12 with bone screw 16 and surgical cables 20, in combination. It is within the scope of the present invention that surgical cables 20 may be used alone, such as when bone 12 is too weak and/or damaged to receive bone screw 16. Each surgical cable includes first end 22 and second end 24. As shown in FIG. 1, first end 22 of each surgical cable 20 includes plug 23. Surgical cables 20 may include multi-strand cables of stainless steel, titanium, cobalt chrome, or another suitable biocompatible material, for example.

In the illustrated embodiment of FIG. 1, bone plate 10 is configured to receive at least one surgical cable 20. More particularly, bone plate 10 includes first transverse bore 26 and an adjacent second transverse bore 28, both of which are configured to receive surgical cable 20. An exemplary orthopedic assembly is the Cable-Ready™ Cable Grip System generally available from Zimmer, Inc. of Warsaw, Ind.

In operation, a surgeon inserts the free, second end 24 of surgical cable 20 into first transverse bore 26 of bone plate 10. Then, the surgeon pulls surgical cable 20 through first transverse bore 26 of bone plate 10 until plug 23 on first end 22 of surgical cable 20 seats in first transverse bore 26. Next, the surgeon wraps second end 24 of surgical cable 20 around shaft 14 of bone 12 to form loop 30, as shown in FIG. 1. This wrapping step may be performed with the help of a cable passer device (not shown). Finally, the surgeon inserts second end 24 of surgical cable 20 into second transverse bore 28 of bone plate 10. At this stage, loop 30 of surgical cable 20 may be placed loosely around bone 12. However, before clamping surgical cable 20 in place, the surgeon should ensure that surgical cable 20 is wrapped tightly around bone 12.

Figure 3:
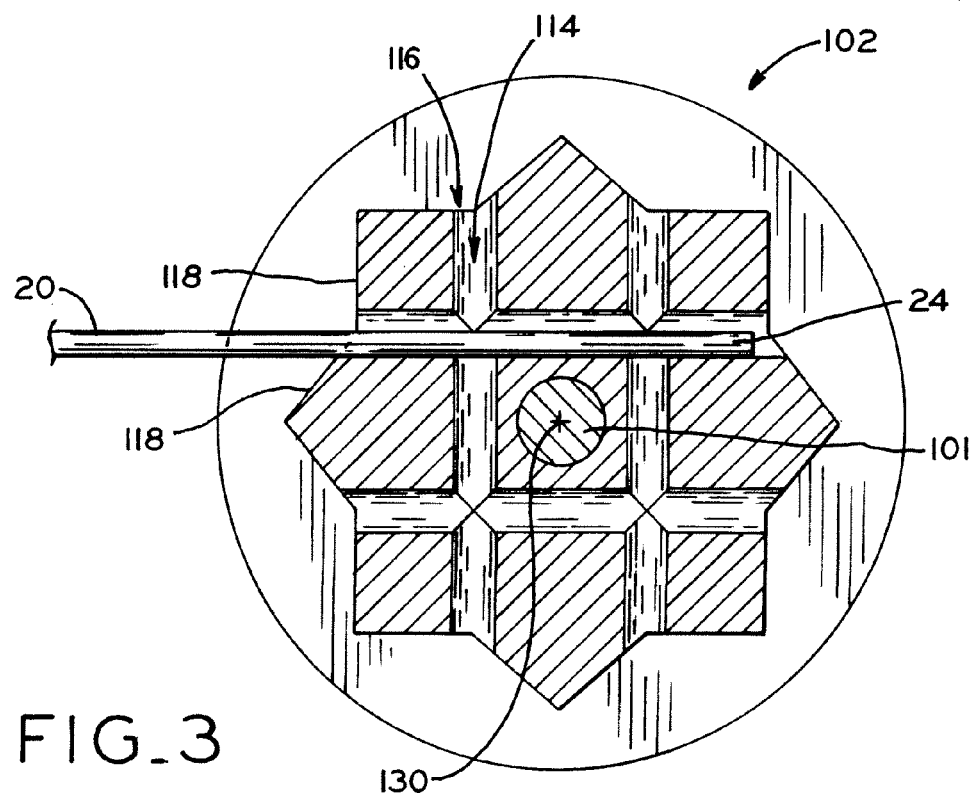
FIG. 3 is a cross-sectional view of the winding drum of FIG. 2, taken along line 3-3 of FIG. 2.
Figure 4:
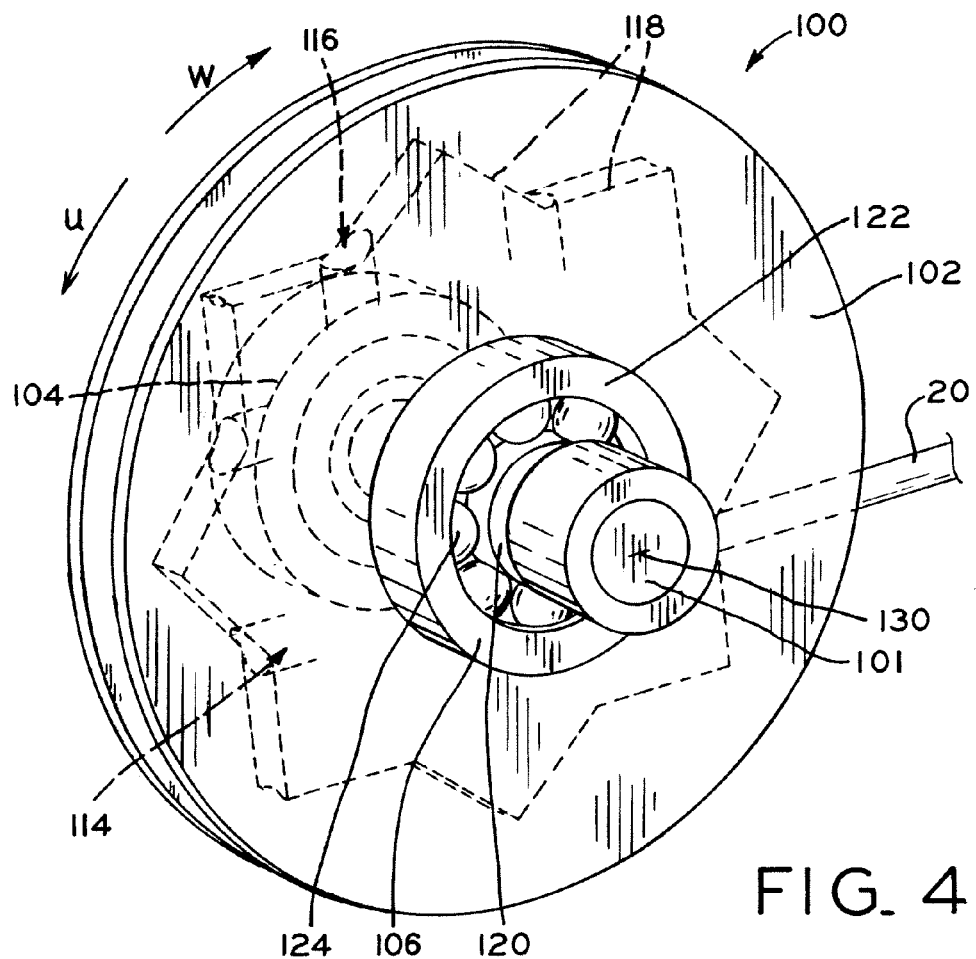
FIG. 4 is a right-side perspective view of the tensioning tool of FIG. 2, further including a one-way lock bearing and a one-way actuator bearing coupled to the shaft.
Figure 5:
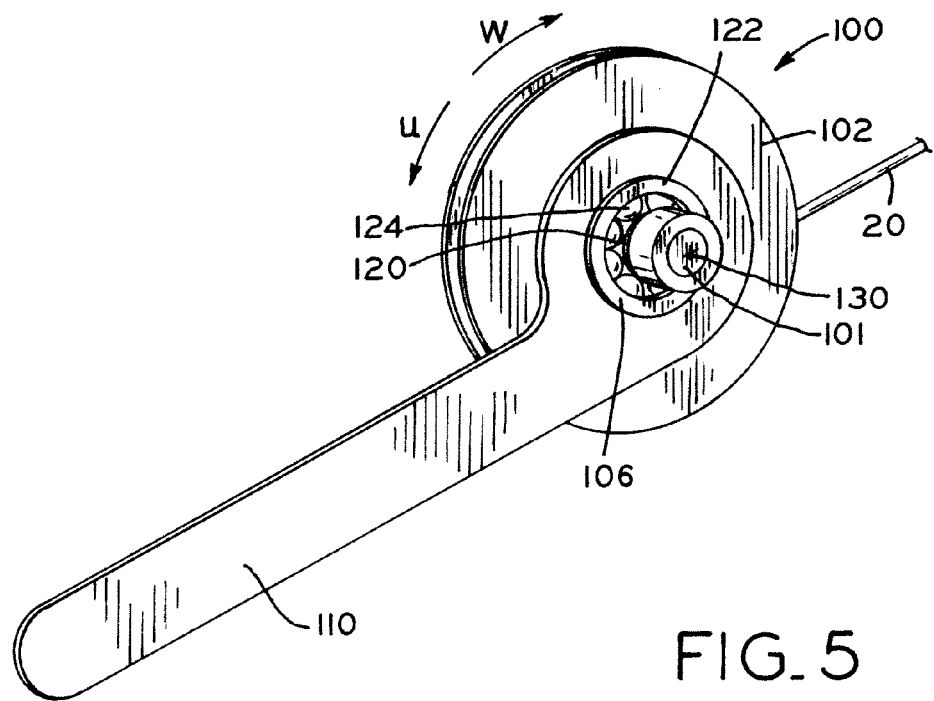
FIG. 5 is a right-side perspective view of the tensioning tool of FIG. 4, further including an actuating lever coupled to the one-way actuator bearing.
Figure 6A:
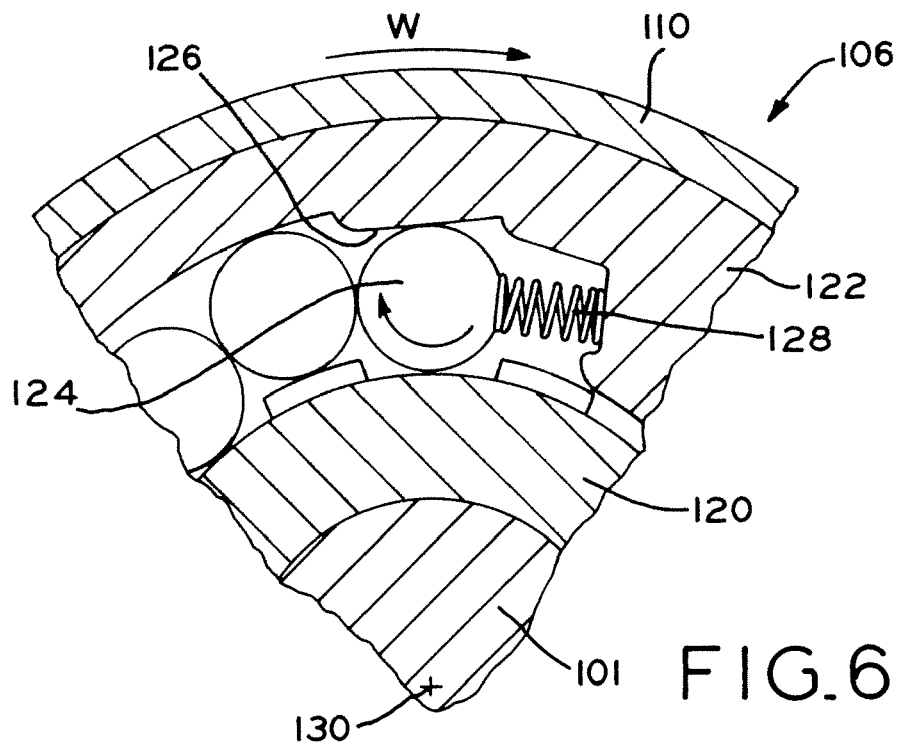
FIG. 6A is a cross-sectional view of the one-way actuator bearing, the actuating lever, and the shaft of FIG. 5, shown with the one-way actuator bearing in a locked position.
Figure 6B:
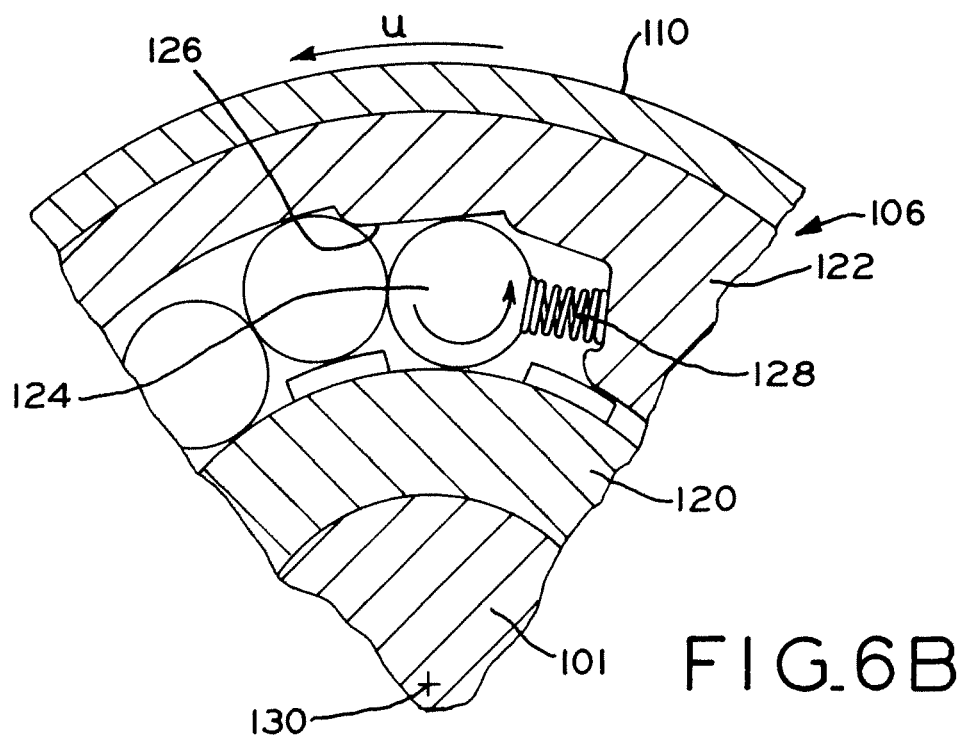
FIG. 6B is another cross-sectional view of the one-way actuator bearing, the actuating lever, and the shaft of FIG. 5, shown with the one-way actuator bearing in an unlocked position.
Figure 7:
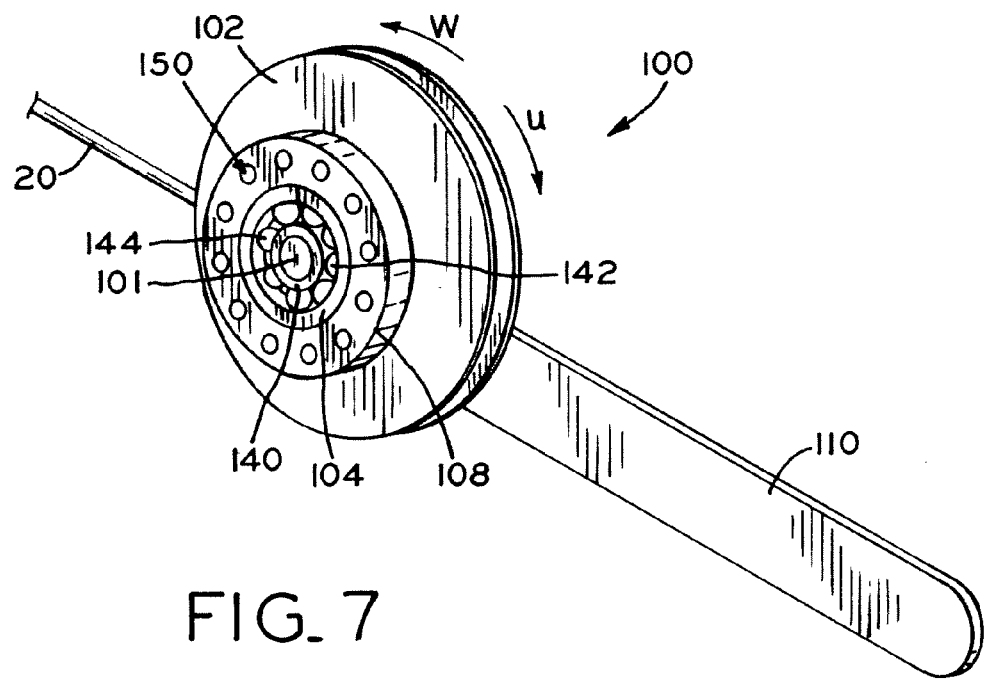
FIG. 7 is a left-side perspective view of the tensioning tool of FIG. 5, further including a locking ring coupled to the one-way lock bearing.
Figure 8:
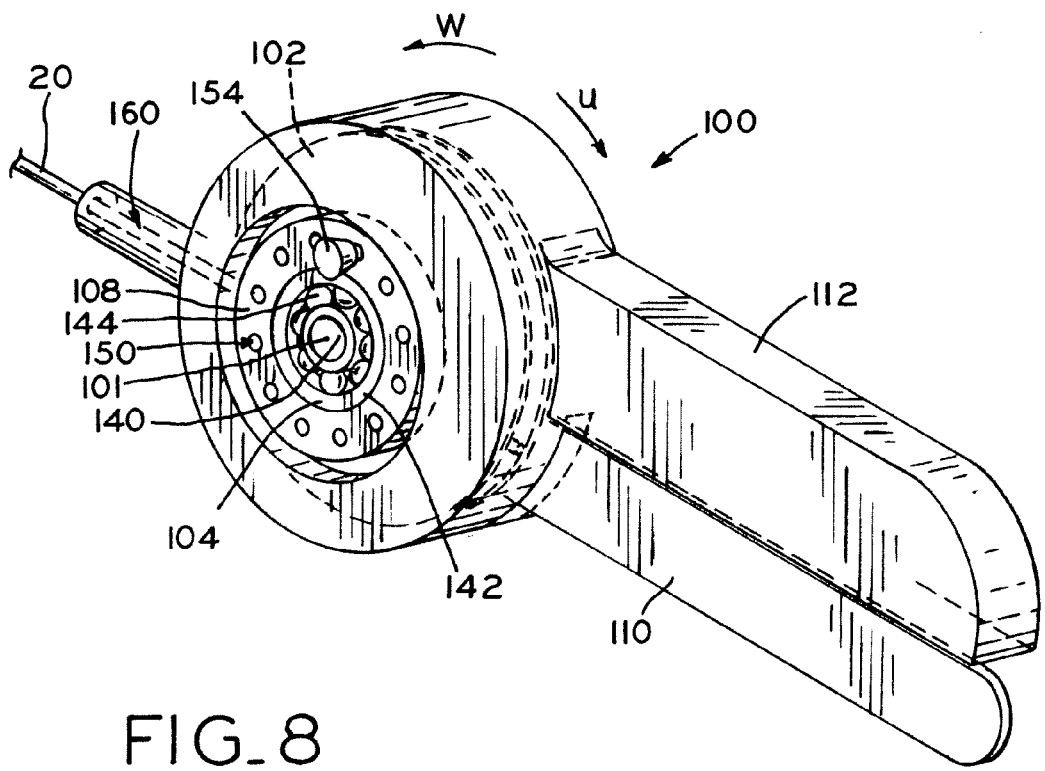
FIG. 8 is a left-side perspective view of the tensioning tool of FIG. 7, further including a housing.

Referring to FIGS. 2-10, tensioning tool 100 is provided to tighten surgical cable 20 to a desired degree of tension around bone 12 (FIG. 1). As shown in FIG. 4, tensioning tool 100 includes shaft 101, winding drum 102, one-way lock bearing 104, and one-way actuator bearing 106. Tensioning tool 100 also includes locking ring 108 coupled to one-way lock bearing 104, as shown in FIG. 7, and actuating lever 110 coupled to one-way actuator bearing 106, as shown in FIG. 5. Tensioning tool 100 further includes exterior housing 112, as shown in FIG. 8. Each component of tensioning tool 100 is described further below.

As shown in FIGS. 10 and 11, housing 112 of tensioning tool 100 substantially surrounds shaft 101, winding drum 102, one-way lock bearing 104, and one-way actuator bearing 106. Shaft 101 is configured to rotate relative to housing 112 about pivot axis 130. Optionally, housing 112 may include window 113 so that a surgeon is able to view and/or access the components located inside housing 112. Housing 112 also includes receiving chamber 160 that is configured to receive surgical cable 20.

As shown next in FIGS. 3 and 4, winding drum 102 of tensioning tool 100 is coupled to shaft 101 for rotation therewith. Winding drum 102 defines a plurality of internal channels 114. In the illustrated embodiment of FIG. 3, internal channels 114 of winding drum 102 are offset from the center of winding drum 102 and intersect within winding drum 102 in a grid-shaped pattern, such that each internal channel 114 is both parallel to and orthogonal to other internal channels 114. In this arrangement, surgical cable 20 is able to extend substantially entirely through winding drum 102 without interfering with shaft 101 in the center of winding drum 102. Winding drum 102 also includes at least one exposed opening 116 into each channel 114 that is accessible by a surgeon. According to an exemplary embodiment of the present invention, openings 116 are spaced radially about the outer circumference of winding drum 102. With openings 116 spaced radially about the outer circumference of winding drum 102, winding drum 102 need not be rotated into a particular orientation with surgical cable 20 to receive surgical cable 20. According to another exemplary embodiment of the present invention, winding drum 102 includes tapered entrance walls 118 at each opening 116 to direct surgical cable 20 into openings 116 and the corresponding channels 114.

In operation, the surgeon inserts second end 24 of surgical cable 20 through receiving chamber 160 of housing 108, through a selected opening 116 of winding drum 102, and into its corresponding internal channel 114. It is within the scope of the present invention that the surgeon may feed surgical cable 20 entirely through internal channel 114 and out the opposite opening 116. It is also within the scope of the present invention that the surgeon may feed surgical cable 20 through more than one internal channel 114 to facilitate securement of surgical cable 20 to winding drum 102. It is further within the scope of the present invention that channel 114 may be sized to frictionally grip surgical cable 20 therein. After inserting surgical cable 20 into internal channel 114, the surgeon bends surgical cable 20 along opening 116 of internal channel 114 and begins to wind surgical cable 20 around the outer circumference of winding drum 102.

As shown next in FIGS. 4 and 5, one-way actuator bearing 106 of tensioning tool 100 is coupled to shaft 101. One-way actuator bearing 106 includes inner bearing race 120, outer bearing race 122, and rollers 124 located between inner bearing race 120 and outer bearing race 122. Inner bearing race 120 of actuator bearing 106 is coupled to shaft 101 for movement therewith, and actuating lever 110 is coupled to outer bearing race 122 of actuator bearing 106 for movement therewith. Also, as shown in FIGS. 6A and 6B, actuator bearing 106 includes clutch surface 126 and spring 128 that biases rollers 124 toward clutch surface 126.

With reference to FIGS. 6A and 6B, an exemplary one-way actuator bearing 106 is oriented on shaft 101 such that actuator bearing 106 locks when inner bearing race 120 is rotated in a counter-clockwise direction or when outer bearing race 122 is rotated in a clockwise direction. In this exemplary arrangement, actuator bearing 106 does not lock when inner bearing race 120 is rotated in a clockwise direction or when outer bearing race 122 is rotated in a counter-clockwise direction.

Actuator bearing 106 is provided to rotate shaft 101 in a first, winding direction W. More particularly, actuator bearing 106 is provided to rotate winding drum 102 coupled to shaft 101 in the winding direction W. In operation, the surgeon lifts actuating lever 110 such that actuating lever 110 and outer bearing race 122 of actuator bearing 106 rotate in the winding direction W about pivot axis 130. As outer bearing race 122 of actuator bearing 106 is forced in the winding direction W, rollers 124 are forced into frictional engagement with clutch surface 126 (e.g. at the bottom end of the ramped surface), as shown in FIG. 6A, and are frictionally locked between outer bearing race 122 and inner bearing race 120. The torque applied to outer bearing race 122 of actuator bearing 106 is then transmitted through the locked rollers 124 to inner bearing race 120 of actuator bearing 106 and shaft 101, causing inner bearing race 120 and shaft 101 to rotate along with outer bearing race 122 in the winding direction W.

The surgeon then releases actuating lever 110, which causes actuating lever 110 to rotate in a second, unwinding direction U and return to its neutral state relative to housing 112. For example, actuating lever 110 may be spring-biased away from housing 112. As actuating lever 110 and outer bearing race 122 of actuator bearing 106 rotate in the unwinding direction U, rollers 124 roll away from clutch surface 126 and roll freely in the space available between inner bearing race 120 and outer bearing race 122 (e.g. at the top end of the ramped surface), as shown in FIG. 6B. Thus, the torque applied to actuating lever 110 and outer bearing race 122 is not transmitted to inner bearing race 120, and, as a result, actuating lever 110 and outer bearing race 122 rotate freely relative to shaft 101 in the unwinding direction U.

As shown next in FIGS. 7 and 8, one-way lock bearing 104 of tensioning tool 100 is coupled to shaft 101. Like actuator bearing 106, lock bearing 104 includes inner bearing race 140, outer bearing race 142, and rollers 144 located between inner bearing race 140 and outer bearing race 142. Inner bearing race 140 of lock bearing 104 is coupled to shaft 101 for movement therewith, and locking ring 108 is coupled to outer bearing race 142 of lock bearing 104 for movement therewith. Also, as shown in FIGS. 9A and 9B, lock bearing 104 includes clutch surface 146 and spring 148 that biases rollers 144 toward clutch surface 146.

Figure 9A:
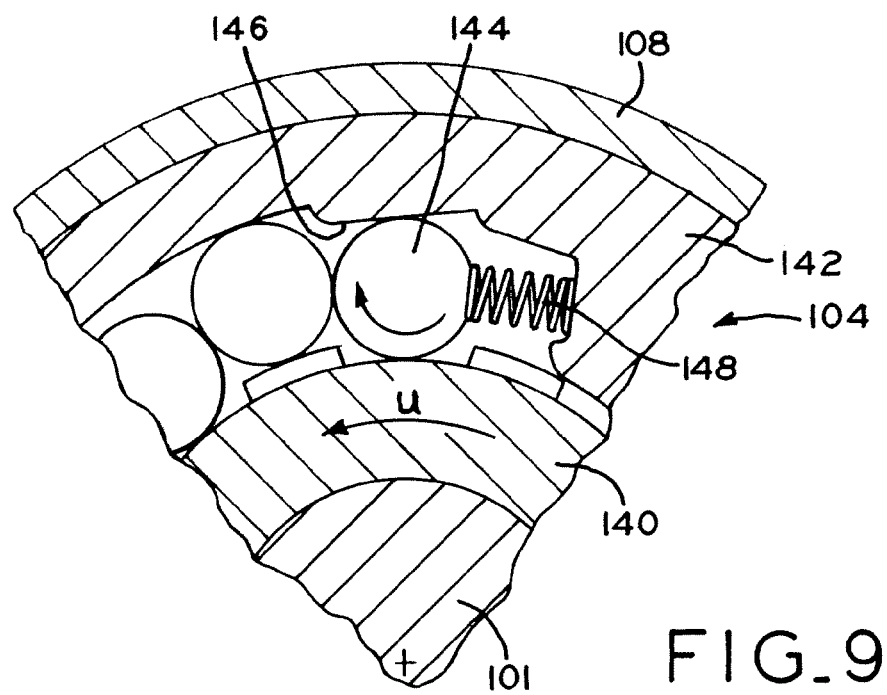
FIG. 9A is a cross-sectional view of the one-way lock bearing, the locking ring, and the shaft of FIG. 7, shown with the one-way lock bearing in a locked position.
Figure 9B:
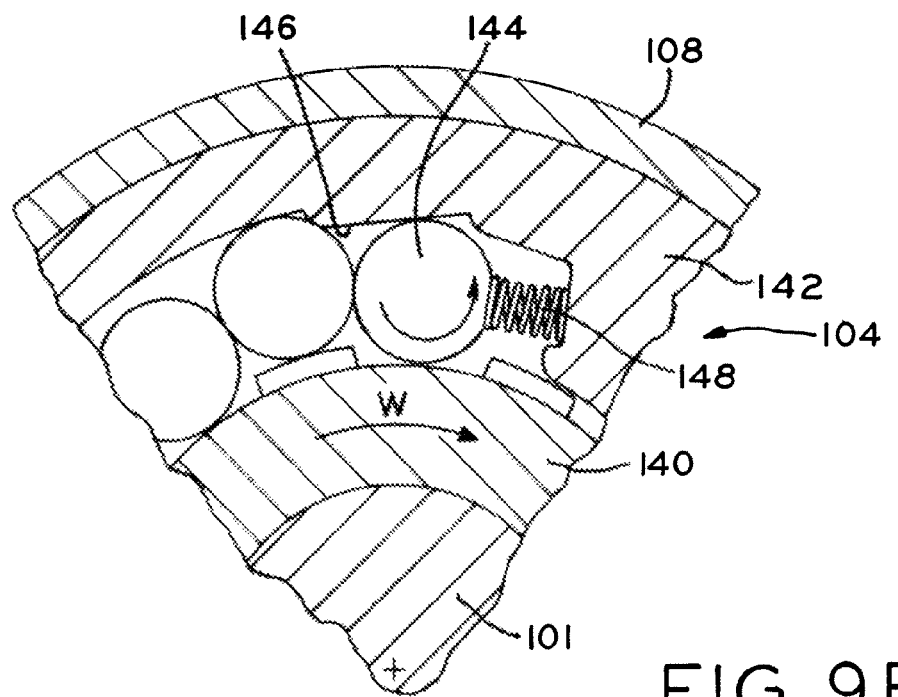
FIG. 9B is another cross-sectional view of the one-way lock bearing, the locking ring, and the shaft of FIG. 7, shown with the one-way lock bearing in an unlocked position.

With reference to FIGS. 9A and 9B, an exemplary one-way lock bearing 104 is oriented on shaft 101 such that lock bearing 104 locks when inner bearing race 140 is rotated in a counter-clockwise direction or when outer bearing race 142 is rotated in a clockwise direction. In this exemplary arrangement, lock bearing 104 does not lock when inner bearing race 140 is rotated in a clockwise direction or when outer bearing race 142 is rotated in a counter-clockwise direction.

Locking ring 108 of tensioning tool 100 may be selectively rotationally locked relative to housing 112. Thus, outer bearing race 142 of lock bearing 104, which is coupled to locking ring 108, may be selectively rotationally locked relative to housing 112. For example, in the illustrated embodiment, locking ring 108 includes a plurality of radially spaced pin apertures 150, as shown in FIG. 8, and housing 112 includes at least one locking aperture 152, as shown in FIG. 10. In operation, a surgeon inserts locking pin 154 through locking aperture 152 in housing 112 and through an adjacent one of the pin apertures 150 in locking ring 108, as shown in FIG. 11, to rotationally lock locking ring 108 relative to housing 112.

Lock bearing 104 is provided to prevent shaft 101 from rotating in the unwinding direction U. More particularly, lock bearing 104 is provided to prevent winding drum 102 coupled to shaft 101 from rotating in the unwinding direction U. As shaft 101 and inner bearing race 140 of lock bearing 104 attempt to rotate in the unwinding direction U, rollers 144 are forced into frictional engagement with clutch surface 146 (e.g. at the bottom end of the ramped surface), as shown in FIG. 9A, and are frictionally locked between outer bearing race 142 and inner bearing race 140. The torque applied to shaft 101 and inner bearing race 140 of lock bearing 104 is then transmitted through the locked rollers 144 to outer bearing race 142 of lock bearing 104. However, as discussed above, outer bearing race 142 of lock bearing 104 and locking ring 108 are coupled to housing 112 and prevented from rotating relative to housing 112. Thus, shaft 101 is also prevented from rotating relative to housing 112.

Lock bearing 104 does not interfere with the rotation of shaft 101 in the winding direction W. As shaft 101 and inner bearing race 140 of lock bearing 104 are rotated in the winding direction W, rollers 144 roll away from clutch surface 146 and roll freely in the space available between inner bearing race 140 and outer bearing race 142 (e.g. at the top end of the ramped surface), as shown in FIG. 9B. Thus, the torque applied to shaft 101 is not transmitted to outer bearing race 142 of lock bearing 104, and, as a result, shaft 101 and inner bearing race 140 of lock bearing 104 rotate freely relative to outer bearing race 144 of lock bearing 104 and locking ring 108, which are rotationally locked to housing 112.

According to an exemplary embodiment of the present invention, lock bearing 104 is identical or substantially similar to actuator bearing 106. For example, lock bearing 104 and actuator bearing 106 may be similar or identical to the one-way clutch mechanism disclosed in U.S. Patent Publication No. 2009/0008205, entitled "ONE-WAY CLUTCH", filed Jul. 2, 2008, the disclosure of which is expressly incorporated by reference herein. Other exemplary one-way bearings are generally available from Stock Drive Products of New Hyde Park, N.Y., and KOYO Corporation of Westlake, Ohio, for example.

According to another exemplary embodiment of the present invention, lock bearing 104 and actuator bearing 106 have the same orientation on shaft 101 of tensioning tool 100. For example, both lock bearing 104 and actuator bearing 106 may be arranged to resist counter-clockwise rotation of shaft 101. However, unlike lock bearing 104 which is configured to respond to interior torque from shaft 101, actuator bearing 106 is configured to respond to exterior torque from actuating lever 110.

In operation, a surgeon wraps surgical cable 20 around winding drum 102 of tensioning tool 100 by repeatedly pressing and releasing actuating lever 110. Referring to FIG. 5, pressing actuating lever 110 upward in the winding direction W causes actuator bearing 106 to engage and rotate shaft 101 in the winding direction W. Actuating lever 110 and actuator bearing 106 are then free to rotate in the unwinding direction U relative to shaft 101 to return to a neutral, starting position. Referring to FIG. 8, shaft 101 is free to rotate in the winding direction W relative to lock bearing 104, but shaft 101 engages the stationary lock bearing 104 when attempting to rotate in the unwinding direction U.

As surgical cable 20 is tightened in tensioning tool 100, surgical cable 20 will be pulled toward bone plate 10 and bone 12 (FIG. 1) in the unwinding direction U. To prevent second end 24 of surgical cable 20 from pulling out of tensioning tool 100, winding drum 102 includes internal channels 114 for receiving surgical cable 20, as discussed above. Also, to prevent tensioning tool 100 from unwinding, lock bearing 104 resists movement of shaft 101 in the unwinding direction U.

After surgical cable 20 is tightened to a desired degree of tension around bone 12, surgical cable 20 is secured in place. For example, as shown in FIG. 1, the surgeon may tighten set screw 32 against surgical cable 20 in second transverse bore 28. Alternatively, the surgeon may clamp opposing ends of loop 30 together using a wire clamp, for example. After securing surgical cable 20 in place, the surgeon may cut excess length from surgical cable 20 such that second end 24 of surgical cable 20 is flush with bone plate 10. In this embodiment, first end 22 of surgical cable 20 is received substantially entirely within first transverse bore 26 of bone plate 10 and second end 24 of surgical cable 20 is received substantially entirely within second transverse bore 28 of bone plate 10 to avoid interfering with adjacent soft tissue.

Referring again to FIGS. 8 and 11, after surgical cable 20 is secured to bone plate 10, the excess surgical cable 20 may be unwound from winding drum 102 by removing locking pin 154 from housing 112 and locking ring 108. Shaft 101 and winding drum 102 will then be free to rotate in the unwinding direction U because outer bearing race 142 of lock bearing 104 and locking ring 108 will be free to rotate relative to housing 112.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tool for tensioning a surgical cable around a bone comprising:
   a housing;
   a shaft;
   a drum configured to rotate in a first winding direction to wind the surgical cable around the drum and in a second unwinding direction to unwind the surgical cable from the drum, the drum defining at least first and second internal channels configured to receive the surgical cable therein, the drum including a first guide wall that angles downward into the first internal channel and a second guide wall that angles downward into the second internal channel, the first and second guide walls intersecting along a peak such that, on a first side of the peak, the surgical cable is guided into the first internal channel by the first guide wall and, on a second side of the peak, the surgical cable is guided into the second internal channel by the second guide wall;

a lock mechanism that prevents the drum from rotating in the second unwinding direction; and an actuator mechanism that rotates the drum in the first winding direction.

2. The tool of claim 1, wherein the drum includes a first opening into the first internal channel and a second opening into the second internal channel, the first and second openings radially spaced across an outer circumference of the drum.

3. The tool of claim 1, wherein first and second internal channels intersect within the drum.

4. The tool of claim 1, wherein first and second internal channels are spaced apart from a center of the drum.

5. The tool of claim 1, wherein the first internal channel extends through the drum in a direction transverse to the second internal channel.

6. The tool of claim 1 further comprising:

wherein the lock mechanism comprises a lock bearing coupled to the shaft and configured to prevent the shaft from rotating in the second unwinding direction relative to the housing; and wherein the actuator mechanism comprises an actuator bearing coupled to the shaft and configured to rotate the shaft in the first winding direction.

7. The tool of claim 6, wherein the lock bearing permits the shaft to rotate in the first winding direction.

8. The tool of claim 6, wherein the lock bearing comprises an inner bearing race coupled to the shaft for movement therewith and an outer bearing race.

9. The tool of claim 8, wherein the outer bearing race locks relative to the inner bearing race to prevent the shaft from rotating in the second unwinding direction.

10. The tool of claim 8, further comprising a locking ring coupled to the outer bearing race of the lock bearing for movement therewith.

11. The tool of claim 10, wherein the locking ring is selectively coupled to the housing to prevent rotation of the outer bearing race relative to the housing.

12. The tool of claim 6, wherein the actuator bearing comprises an inner bearing race coupled to the shaft for movement therewith and an outer bearing race, the outer bearing race locking relative to the inner bearing race to rotate the shaft in the first winding direction.

13. The tool of claim 12, further comprising an actuating lever coupled to the outer bearing race of the actuator bearing for movement therewith.

14. The tool of claim 6, wherein the lock bearing is substantially identical to the actuator bearing.

* * * * *